United States Patent [19]

Matsumoto et al.

[11] Patent Number: 4,995,911
[45] Date of Patent: Feb. 26, 1991

[54] PROCESS FOR RECOVERING UNREACTED SUCROSE FROM REACTION MIXTURE IN SYNTHESIS OF SUCROSE FATTY ACID ESTERS

[75] Inventors: Shusaku Matsumoto, Kyoto; Yoshio Hatakawa, Higashiosaka; Akihiko Nakajima, Kyoto, all of Japan

[73] Assignee: Dai-Ichi Kogyo Seiyaku Co., Ltd., Kyoto, Japan

[21] Appl. No.: 365,644

[22] Filed: Jun. 13, 1989

[30] Foreign Application Priority Data

Jun. 14, 1988 [JP] Japan ................................ 63-146586

[51] Int. Cl.$^5$ .......................... C13D 3/00; C13D 3/16
[52] U.S. Cl. ........................................ 127/48; 127/55; 127/54; 127/53; 536/127; 536/115; 536/119
[58] Field of Search ........................ 127/48, 55, 54, 53; 536/127, 115, 119

[56] References Cited

U.S. PATENT DOCUMENTS

| 3,792,041 | 2/1974 | Yamagishi et al. | |
| 4,611,055 | 9/1986 | Yamamoto et al. | 536/127 |
| 4,710,567 | 12/1987 | Kea et al. | 536/127 |
| 4,810,787 | 3/1989 | Garvey et al. | 536/127 |

FOREIGN PATENT DOCUMENTS

| 35-13102 | 9/1960 | Japan . | |
| 42-8850 | 4/1967 | Japan . | |
| 51-7134 | 1/1976 | Japan | 127/54 |
| 51-29417 | 3/1976 | Japan . | |
| 809815 | 3/1959 | United Kingdom . | |

Primary Examiner—Chung K. Pak
Attorney, Agent, or Firm—Armstrong, Nikaido, Marmelstein, Kubovcik & Murray

[57] ABSTRACT

A process for recovering unreacted sucrose from a reaction mixture of sucrose and a fatty acid alkyl ester in an organic solvent as reaction medium in the presence of a catalyst in the production of a sucrose fatty acid ester which comprises adjusting the reaction mixture from which a part of the organic solvent as reaction medium may be previously removed and to which water is added, to a neutral pH region, adding a neutral salt and sucrose to the reaction mixture to precipitate the sucrose fatty acid ester, filtering off the precipitate, and bringing the filtrate into contact with a reverse osmosis membrane to recover the unreacted sucrose. According to the invention, unreacted sucrose can be easily recovered, while the sucrose fatty acid ester not contaminated with the organic solvent as reaction medium can be obtained from the reaction mixture without using an organic solvent for purification.

10 Claims, 1 Drawing Sheet

PROCESS FOR RECOVERING UNREACTED SUCROSE FROM REACTION MIXTURE IN SYNTHESIS OF SUCROSE FATTY ACID ESTERS

BACKGROUND OF THE INVENTION

The present invention relates to a treatment of a reaction mixture of sucrose and a fatty acid alkyl ester. More particularly, the present invention relates to an industrially useful process for recovering the unreacted sucrose from the reaction mixture obtained in the synthesis of sucrose fatty acid esters in an organic solvent medium.

Sucrose fatty acid esters (sugar esters) useful as surface active agents are prepared industrially at present by either a solvent process wherein sucrose is reacted with a methyl ester of a higher fatty acid having 8 to 22 carbon atoms in the presence of a suitable catalyst in an organic solvent such as dimethylformamide or dimethylsulfoxide, as disclosed in Japanese Pat. Publication Kokoku No. 35-13102; or an aqueous medium process wherein sucrose is formed into a molten mixture with a fatty acid salt (soap) using water without using an organic solvent, and is then reacted with a higher fatty acid methyl ester in the presence of a catalyst, as disclosed in Japanese Pat. Publication Kokoku No. 51-14485. However, even according to any of these processes, the obtained reaction mixture contains impurities such as the unreacted sucrose, the unreacted fatty acid methyl ester, residual catalyst, soap, free fatty acid, volatile material, etc. in addition to the desired sucrose fatty acid ester. These impurities, at least impurities whose contents exceed the specified amounts must be removed prior to being put on the market. Purification according to conventional processes requires a large amount of an organic solvent as purification solvent. On the other hand, removal of the solvent (volatile material) remaining in the product is very important in view of strict regulation, e.g. provision by FDA, U.S.A according to which allowable content of remaining dimethylsulfoxide in sucrose fatty acid esters is at most 2 p.p.m. [Fed. Regist., 51(214), 40160-1]. Removal of the unreacted sucrose is also important because it is included in a large amount in the reaction mixture.

The use of a large amount of solvents conventionally used for purification of sucrose fatty acid esters, in particular, upon industrial production of sucrose fatty acid esters, results in the following disadvantages: (1) risk of explosion and fire, (2) provision of explosion and fire prevention means to electric devices, (3) application of closed system to production equipment for explosion and fire prevention, (4) requirement of fireproof construction for entire building by way of precaution against explosion and fire, (5) rise in fixed cost due to the items (2), (3) and (4), (6) rise in materials cost due to loss of solvent, (7) contamination of the product with remaining solvent, and (8) adverse influence on health of workers, and increase of cost resulting from increase in labor required for the prevention therefor.

In view of these circumstances, it has been desired to develop a purification technique capable of removing the unreacted sucrose and other impurities from the crude reaction mixture without using organic solvents.

Thus, a purification method using no organic solvent has hitherto been studied. For example, as a representative method, there has been known (1) a method wherein a sucrose fatty acid ester is precipitated by addition of an acidic aqueous solution to the reaction mixture, as disclosed in British Pat. No. 809,815 and (2) a method wherein a sucrose fatty acid ester is precipitated by addition of an aqueous solution of a common neutral salt to the reaction mixture, as disclosed in Japanese Pat. Publication Tokkyo Kokoku No. 42-8850.

However, these methods have disadvantages. When an acidic aqueous solution, for example, hydrochloric acid, is added to the reaction mixture as in the method (1), the sucrose fatty acid ester immediately deposits, but the unreacted sucrose is easily decomposed and converted into glucose and fruit sugar. This cannot be avoided even if the addition is conducted at a low temperature (e.g. 0° to 5° C.). Accordingly, the recovery and reuse of the unreacted sucrose become difficult. As is well known, the conversion of sucrose in the synthesis of sucrose fatty acid esters is low. For example, even in the synthesis using dimethylformamide, the conversion of sucrose is at most 50% and, therefore, the recovery of unreacted sucrose is essential from the economical point of view.

Also, the addition of an aqueous solution of a neutral salt such as sodium chloride or Glauber's salt, as in the method (2), causes sucrose fatty acid esters to deposit rapidly. In this case, decomposition of unreacted sucrose does not occur, but the monoester which is an effective component in the product is dissolved in an aqueous phase. Consequently, not only the dissolution results in a large loss of the product, but also it is a hindrance particularly to production of sucrose fatty acid esters having a high HLB which are recently in great demand.

Also, in Japanese Pat. Publication Tokkyo Kokai No. 51-29417, it is proposed to utilize a property that a mixture of water and a solvent used for purification (hereinafter referred to as "purification solvent") separates into an upper light layer and a lower heavy layer. Generally, the lower layer contains a large amount of water and, therefore, the unreacted sucrose, which is hydrophilic, and a salt derived from a catalyst used in the synthesis of sucrose fatty acid esters are dissolved in the lower layer. Since the upper layer contains the purification solvent in a large quantity, compounds having a small polarity such as sucrose fatty acid esters, fatty acids and unreacted fatty acid methyl esters are dissolved in the upper layer. On the other hand, the solvent used for the reaction such as dimethylsulfoxide is dissolved not only in the lower layer, but also inconveniently in the upper layer. Consequently, it is impossible to completely separate the reaction solvent only by this method. In addition, not only the product is contaminated with a trace amount of the reaction solvent, but also a very large amount of the purification solvent is required for removing the unreacted sucrose from the reaction mixture.

In order to industrially realize the purification of crude sucrose fatty acid esters with water, it is very important that the removal of the reaction solvent and the purification solvent is complete and moreover sucrose and the product are not lost.

Another important problem which must also be taken into consideration is a means for recovering the unreacted sucrose incident to the use of water as a purification solvent. Since the purification of the reaction mixture with the use of water is based on difference in water solubility between a sucrose fatty acid ester and unreacted sucrose, migration of a large amount of unreacted sucrose into an aqueous phase cannot be avoided. The manufacture of sucrose fatty acid esters cannot be industrially accepted unless such a dissolved sucrose is recovered. Accordingly, it is also very important to efficiently recover the sucrose which has migrated into an aqueous phase upon purification.

It is a primary object of the present invention to provide a method for recovering unreacted sucrose from the reaction mixture, while removing the reaction solvent without using organic solvents for the purification of the reaction mixture.

The above and other objects of the present invention will become apparent from the description hereinafter.

SUMMARY OF THE INVENTION

The present inventors have made experiments about salting out in order to achieve the following purposes: namely (1) minimizing the amount of sucrose fatty acid esters dissolved in an aqueous phase, and if possible, decreasing it upto zero so as to precipitate the whole of sucrose fatty acid esters, (2) preventing decomposition of unreacted sucrose, (3) separating the reaction solvent from the sucrose fatty acid esters by dissolving the remaining reaction solvent in the aqueous phase, and (4) efficiently recovering the unreacted sucrose from the filtrate (or supernatant) obtained by removing the above-mentioned precipitate. It has now been found that when sucrose and a neutral salt are dissolved in an aqueous solution of the reaction mixture, the whole of the sucrose fatty acid esters is precipitated under a combination of proper pH, temperature, neutral salt, sucrose concentration and amount of water, and moreover, surprisingly, the reaction solvent is dissolved in the aqueous phase with the unreacted sucrose. Thus, it has been found that the remaining volatile material (remaining reaction solvent) can be transferred completely into the aqueous phase, with substantially preventing the loss of sucrose fatty acid esters, by utilizing the above phenomenon, namely by dissolving the precipitated sucrose fatty acid esters again in water and repeating the precipitation procedure by the addition of an aqueous solution of the neutral salt and sucrose, and that the unreacted sucrose can be efficiently recovered from the reaction mixture by contacting the residual liquid after removal of the above precipitate with an adequate reverse osmosis membrane.

In accordance with the present invention, there is provided a process for recovering unreacted sucrose from a reaction mixture in synthesis of a sucrose fatty acid ester by a reaction of sucrose and a fatty acid alkyl ester in an organic solvent, which comprises adjusting the reaction mixture to a neutral pH region, said reaction mixture containing the unreacted sucrose, the unreacted fatty acid alkyl ester, a catalyst, a soap, a fatty acid and a volatile component, adding water, a neutral salt and sucrose to the reaction mixture to precipitate the sucrose fatty acid ester, filtering off the resulting precipitate, and contacting the filtrate with a reverse osmosis membrane.

DETAILED DESCRIPTION

Figure 1:
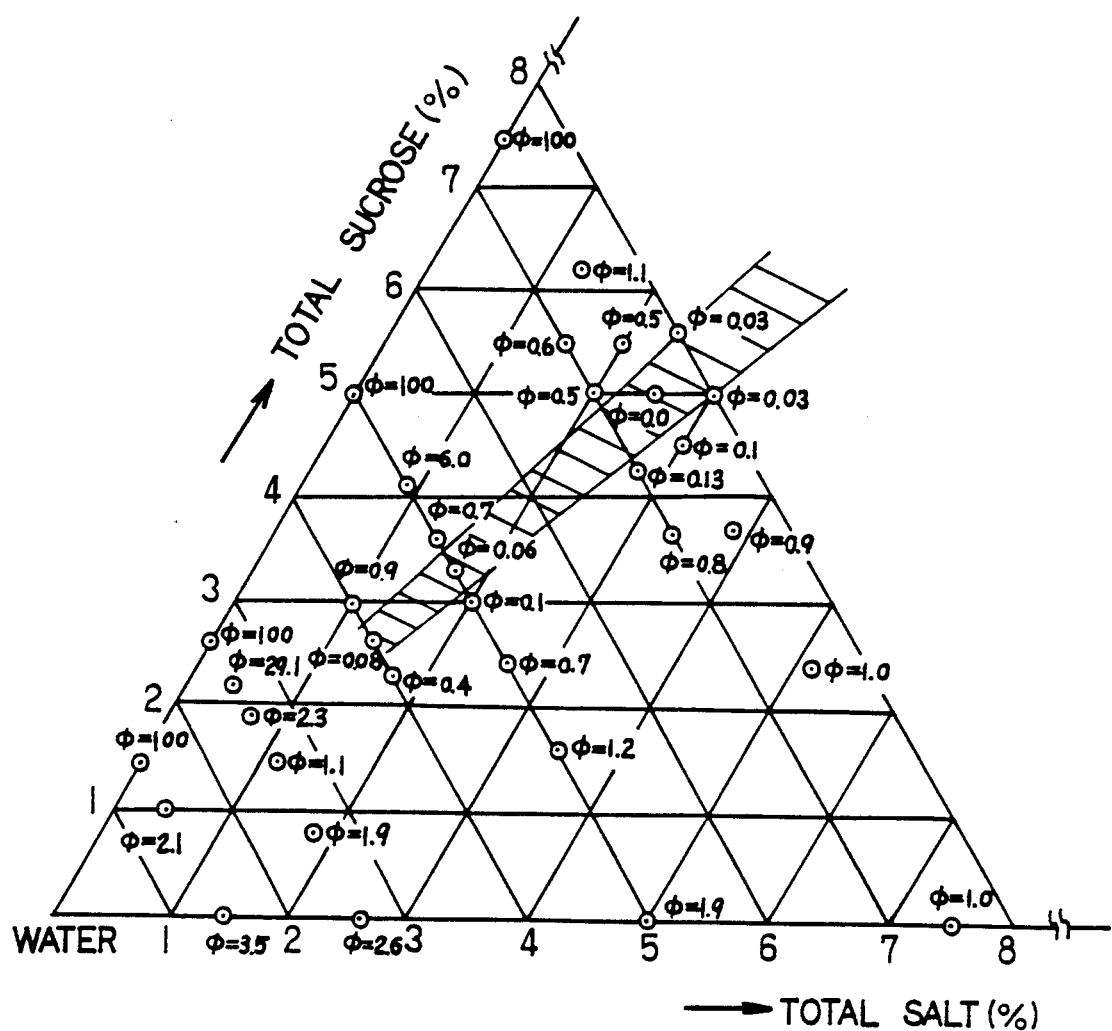
FIG. 1 is a triangular graph showing the relationship between the amount of each of water, total sucrose and total salt, and the amount of sucrose fatty acid ester dissolved in aqueous phase.

The process of the present invention is suitable for purification of the reaction mixture obtained in the synthesis of sucrose fatty acid esters (hereinafter referred to as "SE") by a known reaction using an organic solvent as reaction solvent.

In the synthesis of SE using an organic solvent as reaction medium, generally a reaction solvent, for example, dimethylsulfoxide is added to a mixture of sucrose and a fatty acid methyl ester in an amount of several times the total amount of sucrose and the fatty acid methyl ester to dissolve them. They are reacted in the presence of an alkaline catalyst such as potassium carbonate ($K_2CO_3$) under reduced pressure of 20 to 30 Torrs at a temperature of 80° to 90° C. for several hours, whereby the SE is easily produced in a conversion of at least 90% (based on the fatty acid methyl ester).

In order to deactivate the alkaline catalyst, e.g $K_2CO_3$, included in the resulting reaction mixture, an equivalent amount of an organic acid such as lactic acid or acetic acid, or a mineral acid such as hydrochloric acid or sulfuric acid is added to the reaction mixture. By this neutralization, the catalyst changes to a corresponding salt, e.g. a potassium salt such as potassium lactate, according to the kind of the acid used in the neutralization.

The reaction solvent (e.g. dimethylsulfoxide) is then distilled away under vacuum. The thus obtained residue (reaction mixture after subjected to the neutralization and vaporization of solvent) has approximately the following composition.

| Ingredients | % by weight |
| --- | --- |
| SE | 15.0 to 92 |
| Unreacted sucrose | 1.0 to 80 |
| Unreacted fatty acid methyl ester | 0.5 to 10 |
| Salt derived from $K_2CO_3$ | 0.05 to 7 |
| Soap | 1.0 to 10 |
| Fatty acid | 0.5 to 10 |
| Volatile material (remaining reaction solvent) | 5.0 to 30 |

In that case, the proportion of the monoester in the SE is from 10 to 75% by weight and the proportion of di- and higher esters is from 90 to 25% by weight.

Also, the acid radical mainly included in each of the fatty acid methyl ester, soap and fatty acid is usually a common saturated acid radical having 16 to 22 carbon atoms.

To the reaction mixture from which the solvent is partly distilled away and which has the above-mentioned composition, water is added in a water/reaction mixture ratio of 5:1 to 40:1 by weight, preferably 20:1 by weight, while the pH is adjusted to 6.2 to 8.2, preferably 7.5.

When the ratio of water to the reaction mixture is less than 5, the viscosity of the obtained aqueous solution is high and the following procedures become difficult. Also, when excess water is added to the reaction mixture such that the weight ratio of water to the reaction mixture exceeds 40, the viscosity of the obtained aqueous solution is low and accordingly the following procedures become easy and also the desired removal of reaction solvent can be made well, but a large energy cost is required in removing water upon recovery of unreacted sucrose, etc., thus the economy is impaired.

In order to prevent decomposition of the desired SE, it is preferable to adjust the aqueous solution of the reaction mixture to pH of 6.2 to 8.2. When the pH is more than 8.2, there is a possibility that SE is quantitatively hydrolyzed by an alkali. On the other hand, even in a weak acidic region of less than pH 6.2, there is a fear of acid hydrolysis of SE, for example, when it is exposed to a high temperature over 90° C.

To the thus pH-adjusted aqueous solution of the reaction mixture are added a neutral salt and sucrose, preferably with keeping at a temperature of 50° to 80° C. in order to salt out SE rapidly. In that case, it is preferable that the neutral salt to be added satisfies the following equation (1):

$$\frac{\text{Amount of neutral salt to be added} + \text{Amount of salt formed from catalyst}}{\text{Amount of water} + \text{Total amount of salts} + \text{Total amount of sucrose}} = \tag{1}$$

0.015 to 0.12 by weight wherein the total amount of salts means the sum of the neutral salt to be added and the salt formed by neutralization of the catalyst used in the production of SE, and the total amount of sucrose means the sum of the sucrose to be added and the unreacted sucrose included originally.

Also, it is preferable to add sucrose in an amount satisfying the following equation (2):

$$\frac{\text{Amount of sucrose to be added} + \text{Amount of unreacted sucrose}}{\text{Amount of water} + \text{Total amount of salts} + \text{Total amount of sucrose}} = \tag{2}$$

0.025 to 0.20 by weight

In addition to the above equations (1) and (2), it is also preferable that the total amount of salts and the total amount of sucrose satisfy the following equation (3):

$$\frac{\text{Total amount of salts}}{\text{Total amount of sucrose}} = \begin{array}{l} 0.4 \text{ to } 0.6 \text{ (preferably 0.5)} \\ \text{(preferably 0.5) by weight} \end{array} \tag{3}$$

Representative examples of the neutral salt are, for instance, sodium chloride, Glauber's salt ($Na_2SO_4 \cdot 10H_2O$), potassium lactate and potassium acetate.

It has been found that when the aqueous solution containing SE precipitate obtained by adding neutral salt and sucrose so as to satisfy the equations (1), (2) and (3) is heated to a temperature of 50° to 80° C., approximately the whole amount of SE is precipitated even if the content of the volatile material (remaining reaction solvent) in the reaction mixture widely ranges from 5.0 to 30.0% by weight. This is a peculiar phenomenon and is of important value in connection with the objects of the present invention.

FIG. 1 is a triangular graph showing the above-mentioned phenomenon in more detail. When Y (g) is the weight of SE dissolved in an aqueous phase and X (g) is the weight of SE precipitated, the weight percentage ($\phi$ %) of SE dissolved in the aqueous phase based on the total SE (X+Y) is shown by the following equation:

$$\phi = \frac{Y}{X + Y} \times 100 \; (\% \text{ by weight})$$

The change in the value $\phi$ under the following conditions is shown in the accompanying drawing.

Conditions

Temperature = 80° C.
pH = 7.5
Water/reaction mixture = 7.4/1 by weight
Composition of reaction mixture (% by weight)

| | |
|---|---|
| SE | 29% |
| Unreacted sucrose | 35% |
| Unreacted fatty acid methyl ester | 2% |
| Salt derived from catalyst | 1% |
| Soap | 3% |
| Fatty acid | 1% |
| Volatile material (remaining reaction solvent) | 29% |

Composition of SE (% by weight)
Monoester 73%
Di- and higher esters 27%

In the drawing, the total salt and the total sucrose are as defined above, and the sum of water, total salt and total sucrose is 100% by weight.

The shaded part in FIG. 1 shows the region simultaneously satisfying the equations (1), (2) and (3) which has been discovered by the present inventors.

By adding the determined amounts of sucrose and neutral salt to be dissolved in the aqueous solution of the reaction mixture so as to fall within the shaded region, the volatile material (remaining reaction solvent), salt derived from catalyst, neutral salt added and the whole sucrose are dissolved in the aqueous phase with precipitation of approximately the whole amount of SE, whereby they can be completely separated from the precipitated SE.

The precipitated SE can be recovered by a usual method, for example, by filtration.

It is also important to selectively separate and recover only sucrose from the thus treated aqueous solution from which the precipitated SE has been removed, thus which contains sucrose separated with water, the salt derived from catalyst ($K_2CO_3$), the neutral salt added for salting out and the volatile material. The present inventors have found that utilization of a reverse osmosis membrane is particularly effective for this purpose. After separating the precipitated SE in a usual manner, for example, by filtration, the filtrate is subjected to reverse osmosis.

It is expected that if a fractionation molecular weight ranging from 130 to 200 is selected as that of the reverse osmosis membrane, the unreacted sucrose (molecular weight: 342) and the SE (molecular weight: more than 600) which has incidentally leaked into the filtrate in the prior steps such as the salting out step, would be filtered off without any problem by the reverse osmosis treatment. On the other hand, substances having a molecular weight less than the fractionation molecular weight of 130 to 200, namely the salt derived from catalyst such as potassium lactate (molecular weight: 128), the neutral salt added, and the volatile component such as dimethylsulfoxide (molecular weight: 78) would pass through fine pores of the reverse osmosis membrane without any problem.

As a result of conducting a large number of experiments on the basis of the above presumption, it has been found that when an aqueous solution containing sucrose, the salt derived from catalyst, the neutral salt added in the salting out step and the volatile material, and sometimes further a slight or trace amount of SE, is brought into contact with a reverse osmosis membrane having a fractionation molecular weight of about 150 to about 200 at a temperature of 40° to 60° C. under a pressure, the salt derived from catalyst, the neutral salt and the volatile material easily pass with water through fine pores of the membrane. By this reverse osmosis procedure, low molecular weight substances such as the salts, volatile material and water are separated from the impure aqueous sucrose solution (which may contain a slight amount of SE) to thereby form the concentrated aqueous solution of crude sucrose. An aqueous sucrose solution having a higher purity can be obtained by dissolving the concentrate in fresh water again and subjecting the solution to the reverse osmosis treatment in the same manner, and if necessary, further repeating these procedures.

The temperature of the aqueous solution to be fed to the reverse osmosis is important for obtaining a good result. If the temperature is lower than 40° C., the treating ability is remarkably lowered. Accordingly, it is desired to select a temperature over 40° C. from a practical point of view. On the other hand, it is advisable to conduct the treatment at a temperature below 60° C., since there is a possibility that the heat resistance of the reverse osmosis is changed at a temperature over 60° C. The pH of the aqueous solution to be treated is also important, and the pH ranging from 6.2 to 8.2 is preferred because a fear of influence on the quality of sucrose is minimized.

Recently, various reverse osmosis membranes, which are industrially used and are advanced, have been put on the market from various companies. Among them, for instance, a polyether reverse osmosis membrane is excellent in durability, heat resistance, acid resistance, alkali resistance, fungus resistance, pressure resistance, and the like. Such a membrane is commercially available, for example, under a trade mark "SU-200" from Toray Engineering Kabushiki Kaisha, which has a fractionation molecular weight of about 200 and is suitable to attain the objects of the invention.

In the case of using the reverse osmosis membrane with the fractionation molecular weight of about 200, the treatment of the aqueous solution can be achieved with an industrially acceptable capacity by adjusting the upper limit of the concentration of the solute in the aqueous solution to be supplied to the membrane to 8 to 20% by weight, desirably from about 8 to 15% by weight.

When the solute concentration is more than 15% by weight, it is difficult to pass water, the salt derived from the catalyst and the volatile material through fine pores of the membrane, and accordingly it is obliged to increase a pressure to be applied as the actuation force for reverse osmosis, thus resulting in increase of the area of the reverse osmosis membrane. This is also very uneconomical because of necessity of great electric power. On the other hand, when the aqueous solution contains the solute in a concentration of not more than about 8–15% by weight, it is sufficiently possible to industrially isolate sucrose.

For example, when passing an aqueous solution having the composition shown in Table 1 through the reverse osmosis membrane "SU-200" with an effective area of 8 m² per unit at 50° C. and pH 7.5 and under a pressure applied as the actuation force for reverse osmosis of 56.0 kg/cm²G, the sucrose isolation velocity of 7.3 kg/hour is achieved. Other reverse osmosis membranes similar to "SU-200", commercially available from companies other than Toray Engineering Kabushiki Kaisha, also give similar results. In any cases, SE dissolved in the aqueous solution can be recovered in a good yield together with sucrose.

TABLE 1

| Component | Weight (kg) |
| --- | --- |
| Sucrose fatty acid ester (stearate) | 0.4 |
| Sucrose | 39.0 |
| Potassium lactate | 9.0 |
| Volatile material (reaction solvent) | 5.0 |
| Soap and fatty acid | 0.1 |
| Subtotal | 53.5 |
| Water | 481.0 |
| Total | 534.5 |

Like this, by repeating the reverse osmosis membrane treatment, the salt derived from the catalyst, the added neutral salt and the volatile material are sufficiently removed from the aqueous solution. The thus obtained aqueous solution containing sucrose can keep a sucrose concentration of about 15 to 20% by weight. It is economically disadvantageous as well as technical difficulty to obtain the aqueous solution of sucrose with a concentration of more than 20% by weight by the reverse osmosis means. Accordingly, when it is desired to obtain the aqueous solution of sucrose having a sucrose concentration of more than 20% by weight, the solution is concentrated by using a usual concentration apparatus such as a multiple effect evaporator to adjust to the desirable concentration such as not less than 50% by weight. Thus recovered sucrose can be reused to the preparation of SE as a raw material or used for other purposes.

The following effects can be produced by the process of the present invention. That is to say, in the process of the invention, to the reaction mixture containing unreacted sucrose, unreacted fatty acid methyl ester, catalyst, fatty acid salt (soap), fatty acid and volatile material (remaining reaction solvent) is added an acid to adjust the pH of the reaction mixture to a neutral region, to which water, a neutral salt and sucrose are added, and it is subjected to salting out at a suitable temperature range to transfer the volatilve material (remaining reaction solvent) into the aqueous layer as well as to precipitate the sucrose fatty acid ester, the unreacted fatty acid methyl ester, the soap and the fatty acid. Accordingly, the remaining volatile material can be removed without using organic solvents from the crude reaction mixture. Particularly, when operating the salting out so as to satisfy the conditions shown in the formula (1), the formula (2) and the formula (3), the remaining reaction solvent can be removed without substantial loss of SE. Then, by treating the aqueous phase with the reverse osmosis membrance, only the unreacted sucrose can be selectively recovered in a purity sufficiently high to reuse it, separating the salt derived from the catalyst, the neutral salt used for salting out and the volatile material.

The present invention is more specifically described and explained by means of the following Examples in which all % are by weight unless otherwise noted. It is to be understood that the present invention is not limited to these Examples.

EXAMPLE 1

A reaction solvent was distilled away from a reaction mixture containing SE, unreacted sucrose and methyl stearate obtained according to the solvent method, to give a residue having the composition shown in Table 2.

TABLE 2

| Ingredients | Amount (%) | (kg) |
|---|---|---|
| SE stearate* | 35.2 | 35.2 |
| Unreacted sucrose | 37.5 | 37.5 |
| Unreacted fatty acid methyl ester (stearate) | 1.5 | 1.5 |
| Potassium carbonate | 1.2 | 1.2 |
| Soap | 2.1 | 2.1 |
| Stearic acid | 1.3 | 1.3 |
| Dimethylsulfoxide (reaction solvent) | 21.2 | 21.2 |
| Total | 100 | 100 |

(Note):
*The stearate had a monoester content of 70% and a di- or higher-ester content of 30%.

After neutralizing the residue with lactic acid, it was dried. To 100 kg of the dried matter was added 1,000 kg of water to dissolve it.

To the obtained aqueous solution were added 62.5 kg of sucrose and 97.6 kg of 50% potassium lactate and the temperature thereof was elevated to 75° C. After the precipitated cake was filtered off from the reaction mixture, it was dried at 80° C. in a vacuum. The composition of the dried cake are shown in Table 3. The cake had a water content of 45%.

TABLE 3

| Ingredients | Amount % | kg |
|---|---|---|
| SE | 79.5 | 35.0 |
| Unreacted fatty acid methyl ester | 3.4 | 1.5 |
| Soap | 4.8 | 2.1 |
| Fatty acid | 3.0 | 1.3 |
| Dimethylsulfoxide | 2.5 | 1.1 |
| Sucrose | 5.8 | 2.5 |
| Others | 1.0 | 0.5 |
| Total | 100 | 44.0 |

Measurement of the filtrate according to gel permeation chromatography (GPC) indicated that there was no SE in the filtrate and that 95% of dimethylsulfoxide used as the reaction solvent was removed from the precipitated cake.

Water was added to 1,180 kg of the thus obtained filtrate (aqueous solution containing sucrose, the salts and the volatile material but no SE) to give an aqueous solution having the composition shown in Table 4.

TABLE 4

| Ingredients | Amount % | kg |
|---|---|---|
| SE | 0.01 | 0.2 |
| Sucrose | 5.83 | 97.5 |
| Potassium lactate | 2.96 | 49.5 |
| Dimethylsulfoxide | 1.20 | 20.1 |
| Subtotal | 10.00 | 167.3 |
| Water | 90.00 | 1505.7 |
| Total | 100.00 | 1673.0 |

The aqueous solution was heated to 50° to 52.5° C., and was fed to a reverse osmosis membrane "SU-200" (Toray's trade mark) having a diameter of 4 inches, a length of 1 m and a filtrating area of 8 m² under a pump pressure of 58.2 kg/cm²G under the following operation conditions.

Discharge velocity of the aqueous solution passed throught the reverse osmosis membrane: 3.9 to 2.2 l/minute.

Circulation velocity inside the membrane: 19.2 to 20.9 l/minute.

Feeding time: about 550 minutes.

The concentrate which was not passed through the membrane contained sucrose, the salt derived from the catalyst and the volatile material in amounts of almost all, 46.0% and 52.0% of those included in the original reaction mixture, respectively. The composition of the concentrate is shown in Table 5.

On the other hand, the aqueous solution containing the salt derived from the catalyst and the volatile material, which was passed through the membrane had the composition shown in Table 5. As shown in Table 5, the filtrate scarcely contained sucrose, and contained the salt derived from the catalyst and the neutral salt and the volatile material in amounts of 54.0% and 48.0% of those included in the original reaction mixture, respectively.

TABLE 5

| Ingredients | Filtrate kg | % | Concentrate kg | % |
|---|---|---|---|---|
| SE | 0.0 | 0.0 | 0.2 | 0.2 |
| Unreacted sucrose | 0.0 | 0.0 | 97.5 | 74.4 |
| Potassium lactate*1 | 26.7 | 73.5 | 22.8 | 17.4 |
| DMSO*2 | 9.6 | 26.5 | 10.5 | 8.0 |
| Subtotal | 36.3 | 100 | 131.0 | 100 |
| Water | 588.7 | | 917.0 | |
| Total | 625.0 | | 1048.0 | |

(Note)
*1The salt derived from the catalyst
*2Dimethylsulfoxide (reaction solvent)

EXAMPLE 2

To 1,048 of the concentrate (solute concentration: 12.5%) having the composition shown in Table 5, obtained in Example 1 was added 1,900 kg of water and the thus obtained aqueous solution was fed into the same reverse osmosis membrane as used in Example 1 under the same conditions as in Example 1 to isolate sucrose.

The results are shown in Table 6.

TABLE 6

| Ingredients | Filtrate kg | % | Concentrate kg | % |
|---|---|---|---|---|
| SE | 0.0 | 0.0 | 0.2 | 0.02 |
| Unreacted sucrose | 0.0 | 0.0 | 97.5 | 96.13 |
| Potassium lactate | 15.7 | 68.2 | 7.1 | 0.70 |
| DMSO | 7.3 | 31.8 | 3.2 | 3.15 |
| Subtotal | 23.0 | 100.0 | 108.0 | 100.00 |
| Water | 1909.8 | | 907.2 | |
| Total | 1932.8 | | 1015.2 | |

EXAMPLE 3

To 1,015.2 kg of the concentrate (solute concentrate: 10.6%) shown in Table 6, obtained in Example 2 was added 2,200 kg of water and the thus obtained aqueous solution was fed into the same reverse osmosis membrane as used in Example 1 under the same conditions as in Example 1 to isolate sucrose. The results are shown in Table 7.

TABLE 7

| Ingredients | Filtrate kg | % | Concentrate kg | % |
|---|---|---|---|---|
| SE | 0.0 | 0.0 | 0.1 | 0.1 |
| Unreacted sucrose | 0.0 | 0.0 | 97.4 | 97.0 |

TABLE 7-continued

| Ingredients | Filtrate | | Concentrate | |
|---|---|---|---|---|
| | kg | % | kg | % |
| Potassium lactate | 5.3 | 71.6 | 1.8 | 1.8 |
| DMSO | 2.1 | 28.4 | 1.1 | 1.1 |
| Subtotal | 7.4 | 100.0 | 100.4 | 100 |
| Water | 2197.4 | | 910.0 | |
| Total | 2204.8 | | 1010.4 | |

In addition to the ingredients used in the Examples, other ingredients can be used in the Examples as set forth in the specification to obtain substantially the same results.

What we claim is:

1. A process for recovering unreacted sucrose from the reaction mixture produced in the synthesis of a sucrose fatty acid ester by a reaction of sucrose and a fatty acid alkyl ester in an organic solvent, said reaction mixture containing an unreacted fatty acid alkyl ester, a catalyst, a soap, a fatty acid and a volatile component which comprises steps of:
(a) adjusting the reaction mixture to a substantially neutral pH between 6.2 and 8.2;
(b) adding water, a neutral salt and sucrose to the reaction mixture in amounts satisfying the following equations:

$$\frac{x}{x+y+z} = 0.015 \text{ to } 0.12,$$

$$\frac{y}{x+y+z} = 0.025 \text{ to } 0.20,$$

and $$\frac{x}{y} = 0.4 \text{ to } 0.6$$

wherein, x is an amount which is the sum of the neutral salt to be added and the salt formed by neutralization of catalyst used in the synthesis of sucrose fatty acid ester, y is an amount which is the sum of sucrose to be added and the unreacted sucrose present from the beginning, and z is the total amount of water to precipitate the sucrose fatty acid ester;
(c) filtering off the resulting precipitate; and
(d) enriching the recovered sucrose by contacting the filtrate with a reverse osmosis membrane, wherein said membrane has a fractionation molecular weight of 150 to 200 and wherein said filtrate is maintained at a pH of 6.2 and 8.2 and at temperature of 40° to 60° C. during contact with the membrane.

2. The process of claim 1, wherein the reaction mixture subjected to pH adjustment is maintained at a temperature of 50° to 80° C.

3. The process of claim 1, wherein said water is added to the reaction mixture in a water/reaction mixture ratio of 5:1 to 40:1 by weight.

4. The process of claim 1, wherein the pH adjustment of the reaction mixture is made with an acid selected from the group consisting of lactic acid, acetic acid, hydrochloric acid and sulfuric acid.

5. The process of claim 1, wherein said reaction mixture to be treated consists essentially of 15.0 to 92.0% by weight of a sucrose fatty acid ester, 1.0 to 80.0% by weight of unreacted sucrose, 0.5 to 10.0% by weight of unreacted fatty acid methyl ester, 0.05 to 7.0% by weight of a catalyst, 1.0 to 10.0% by weight of a soap, 0.5 to 10.0% by weight of a fatty acid and 5.0 to 30.0% by weight of a remaining reaction solvent.

6. The process of claim 1, wherein the fatty acid radical included in each of the fatty acid alkyl ester, soap and fatty acid is a saturated fatty acid radical having 16 to 22 carbon atoms.

7. The process of claim 1, wherein said volatile component is dimethylsulfoxide or dimethylformamide.

8. The process of claim 1, wherein said neutral salt to be added to the reaction mixture is a salt selected from the group consisting of sodium chloride, Glauber's salt, potassium lactate and potassium acetate.

9. The process of claim 1, wherein said sucrose fatty acid ester consists of 10 to 75% by weight of the monoester and 90 to 25% by weight of the di- and higher esters.

10. The process of claim 1, wherein said membrane is made of a polyether.

* * * * *